United States Patent [19]
Teisseire et al.
[11] 4,229,323
[45] Oct. 21, 1980

[54] NOR-DEHYDROPATCHOULOL

[75] Inventors: Paul J. Teisseire; Pierre Maupetit, both of Grasse, France
[73] Assignee: Societe Anonyme Roure Bertrand Dupont, Argenteuil, France

[21] Appl. No.: 283,152
[22] Filed: Aug. 23, 1972
[30] Foreign Application Priority Data
Sep. 1, 1971 [FR] France ........ 71.31577
[51] Int. Cl.[3] ........ C07C 35/37; C11B 9/00; C11B 9/02
[52] U.S. Cl. ........ 252/522 R; 568/817; 252/89.1; 252/108
[58] Field of Search ........ 260/617 F; 424/343; 252/522, 108, 89.1; 568/817

[56] References Cited

PUBLICATIONS

Buchi et al., J.A.C.S., vol. 83, pp. 927–938 (1961).
Corey, et al., Science, vol. 166, pp. 178–192 (1969).

*Primary Examiner*—Bernard Helfin
*Assistant Examiner*—James H. Reamer
*Attorney, Agent, or Firm*—Wallenstein, Spangenberg, Hattis & Strampel

[57] ABSTRACT

Nor-dehydropatchoulol having the formula I is disclosed.

I

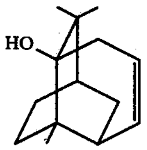

This previously unknown compound has been extracted from natural Patchouli Oil. It can be used in odorant compositions such as perfumes, detergents, aerosols, cosmetic products, etc.

5 Claims, No Drawings

NOR-DEHYDROPATCHOULOL

This invention relates to a novel nor-sesquiterpene compound. In particular it relates to a hitherto unknown, tricyclic nor-sesquiterpene alcohol having the structural formula

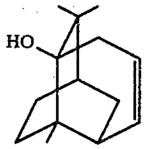

I

This compound of formula I is referred to herein as 'nor-dehydropatchoulol', the name being chosen by analogy with the name patchoulol, which is also referred to as Patchouli alcohol (See Proc. Chem. Soc. 1963 p. 383).

Nor-dehydropatchoulol is a hitherto unknown compound which has been found to exist in the essential oil known as Patchouli Oil (See J.A.C.S. 83 p. 927). We have succeeded in extracting a compound from Patchouli Oil which we have identified as nor-dehydropatchoulol. We have determined that nor-dehydropatchoulol is present in natural Patchouli Oil only to the extent of from about 3 to 10 parts per thousand parts by weight.

The present invention also relates to a process for extracting, from Patchouli Oil, nor-dehydropatchoulol free from impurities such as those found in Patchouli Oil, and to the preparation of perfume compositions to which said extracted nor-dehydropatchoulol has been added. According to one aspect of the invention there is thus provided a process for the extraction of nor-dehydropatchoulol, having the structural formula I given above, which comprises extracting said nor-dehydropatchoulol from Patchouli Oil by physical extraction methods.

The extraction is conveniently carried out by means of several alternative procedures. Physical as well as chemical separation methods may also be employed. Extraction methods which may be used include fractional distillation, thin layer chromatography, gas-liquid partition chromatography, adsorption chromatography, sublimation and/or by combinations of these methods. One preferred method involves fractional distillation of natural Patchouli Oil, collection of the relevant fractions, adsorption chromatography of these fractions on a silica gel column followed by preparative gas-liquid partition chromatography.

Nor-dehydropatchoulol, extracted as described above, followed by purification, e.g. by sublimation, is a white crystalline solid having a melting point of 180 to 183° C., an $[\alpha]_D$ in chloroform of +61.5° and which has the infra-red spectrum and other physical characteristics set out in the following Example. The structure has been confirmed to be that set out in formula I given above by a variety of methods, including chemical degradation and X-ray analysis of derivatives.

Natural Patchouli Oil contains numerous other compounds, including a wide variety of hydrocarbons, epoxides, alcohols and sesquiterpene ketones many of which are also odoriferous compounds. The odour of all these extraneous compounds is of course absent from the odour of pure nor-dehydropatchoulol. Nor-dehydropatchoulol free or essentially free from these other compounds thus constitute a further feature of the present invention.

Nor-dehydropatchoulol has, both in the solid state and in solution in organic solvents such as are normally used in perfumery, an intense odour which is basically of the same type as the odour of natural Patchouli Oil, but is free from the odours of the other odoriferous components of Patchouli Oil and in particular from the odours of the terpenes present in Patchouli Oil. The odour of the pure compound of this invention thereby avoids many of the nuances of the natural essential oil, the odour is furthermore much more stable, and the compound thus constitutes a valuable addition to the arsenal of the perfumer. Nor-dehydropatchoulol gives a distinctly more accentuated musty note and a better light woody note to perfumes than can be obtained with the use of Patchouli Oil. Furthermore, very much smaller amounts of nor-dehydropatchoulol need be added to a perfume formulation as compared with the amount of natural Patchouli Oil which would be needed to obtain the same effect. This latter point is of great importance when the formulation of perfumes and the perfuming of products such as soaps and other toilet products is considered.

Nor-dehydropatchoulol may be used for perfuming products which have hitherto been given an odour using natural Patchouli Oil. It may with advantage be used in many perfumes and also for perfuming industrial products, for example, solid and liquid detergents, synthetic washing agents, aerosols or cosmetic products of all kinds (e.g. soaps). The amount in which nor-dehydropatchoulol can usefully be used in odourant compositions such as for example perfumed products varies over a wide-range. Nor-dehydropatchoulol may thus for example be incorporated into products in an amount of from 1.0 to 20% by weight and preferably from 2.0 to 5.0% by weight.

The extraction of nor-dehydropatchoulol from natural Patchouli Oil and the use of nor-dehydropatchoulol in perfume formulations will now be illustrated with reference to the following Examples.

EXAMPLE 1

5 kg of essential Patchouli Oil from Singapore obtained from the leaves of Pogostemon cablin Benth. (Syn. P. patchouli Pellet var. suavis Hook), were dissolved in 5 liters of diethyl ether. This solution was extracted nine times with 250 ml of 0.06 N aqueous hydrochloric acid. The solution was then washed neutral with diethyl ether. The washed and dried oil which resulted was then carefully fractionated under a reduced pressure of 0.2 to 0.5 mm of mercury using an efficient adiabatic column filled with metal pellets and equipped with a total condensation head. The first 35% of the total weight of distillate were rejected. The fractions rejected in this way had the following physical constants b.p.=80–90° C. (0.3 mm Hg)

$n_D^{15}$=1.5010–1.5070

$\alpha_D$=−50° at 0° C.

The next 15% by weight of the oil collected was the fraction required and had the physical constants b.p.=90–100° C. (0.3 mm Hg)

$n_D^{15}$=1.5070–1.5090

$\alpha_D$=70°.

This latter fraction was then chromatographed on ten times its weight of silica gel (0.05–0.2 mm). The column was first eluted with petroleum ether in order to eliminate residual sesquiterpene hydrocarbons, and then with a mixture of petroleum ether and diethyl ether in ratio of 9:1 by volume.

Repeated chromatography according to the conditions set out above yield a series of fractions enriched in nor-dehydropatchoulol. Traces of epoxy caryophyllene and patchoulol were amongst other constituents present which contaminated the product. The separation on a silica column gel was followed by examination of the different fractions by thin layer chromatography an silica. Using an elution mixture of petroleum ether-/ethyl acetate, 9/1 vol/vol, nor-dehydropatchoulol displayed an $R_F$ of about 0.47.

Preparative gas chromatography effected on the previously enriched fractions obtained as above yielded a white crystalline product which was homogeneous both in gas and thin-layer chromatography.

The product displayed the following physical characteristics: Melting point=180–183° C.; $[a]_D$ in chloroform =61.5°; empirical formula by microanalysis $C_{14}H_{22}O$; molecular weight: 206. Mass spectrum analysis gave the following peaks: 206 (M), 191 (M-$CH_3$), 188 (M-$H_2O$), 173 (188-$CH_3$), 163 (M-$C_3H_7$), 145 (188-$C_3H_7$ or 163-$H_2O$), 119, 107 and 91.

Ultra-violet spectrum (EtOH): no absorption.

Spectrum in the far ultra-violet (n-hexane): $\lambda max = 180$ nm ($\epsilon = 8200$).

I.R. spectrum:

| | | |
|---|---|---|
| $\upsilon\ max^{(cm-1)}$ : | 3620 ($\upsilon$ OH free)<br>3500 ($\upsilon$ OH assoc.)<br>1050 ($\upsilon$ C—O) | (HO—C—) |
| | 1388–1370 ($CH_3$: gem-dimethyl) | |
| | 1650 ($\upsilon$ C=C)<br>1700 ($\gamma$ CH strong) | (—CH=CH—)<br>C |

Associated bands at 1420, 1362, 1288, 1185, 973, 852 and 845.

NMR spectrum at 100 mHz: (solvent $CCl_4$, internal reference TMS) $\delta$(p.p.m.):

0.78 (3 H; S; $(CH_3-\overset{|}{\underset{|}{C}}-)$)

1.06 (2 × 3 H; S; $CH_3-\overset{|}{\underset{|}{C}}-CH_3$)

2.33 (1 H; doublet of doublet; $J_1 \sim 18$ Hz, $J_2 \sim 4$ Hz); (—C$\underline{H}$—CH=CH—)

5.44–5.70 (2 H; J 10 Hz); (C$\underline{H}$=CH—)

The structure of the compound was also confirmed as being that of formula I by means of X-ray analysis on a bromo derivative thereof.

Examples 2 and 3 hereafter illustrate two odoriferous compositions according to the invention containing nor-dehydropatchoulol.

The classical concentrate composition of Example 2 containing 1% by weight of nor-dehydropatchoulol has an odour which emphasises that nor-dehydropatchoulol is free from many unwanted perfumes notes which are present in natural Patchouli oil.

In the composition of Example 3 the introduction of 5% by weight of nor-dehydropatchoulol gives entirely new effects which are unobtainable with natural Patchouli oil.

EXAMPLE 2

| Concentrate No. 1 | Parts by weight |
|---|---|
| Bergamotte peel oil extra | 30 |
| Lemon peel oil | 20 |
| Ylang Ylang oil Nossi-Bé | |
| ethoxyvinyl)-3,3,5,5-tetramethylcyclohexanone | |
| Phenylethyl alcohol | 266 |
| Hydroxycitronellal | 100 |
| Cyclamen aldehyde, 10% in ethyl phthalate (E.P.) | 10 |
| C.10 aldehyde 100%, 10% in E.P. | 5 |
| C.11 aldehyde 100%, 10% in E.P. | 5 |
| Lauraldehyde C.12, 50% in E.P. | 20 |
| Petitgrain oil Citronnier | 10 |
| Benzyl acetate | 60 |
| Phenylacetic acid 1% | 10 |
| Isoeugenol | 20 |
| Linalol | 20 |
| Rose oil Anatolian | 30 |
| Geraniol | 20 |
| Jasmine absolute | 140 |
| Liquid indolene 50% in E.P. | 20 |
| Oak moss absolute A | 60 |
| Forest moss absolute | 20 |
| Methylionone | 50 |
| Florentine iris resinoid, washed | 10 |
| Phenylethyl acetate | 10 |
| Vetiver oil rectified | 20 |
| Vetiveryl acetate | 100 |
| Caryophyllenyl acetate | 60 |
| Guaiacum wood oil | 60 |
| Musk ambrette | 40 |
| Musk ketone | 20 |
| Coumarin | 20 |
| Cyclohexadecanolide | 50 |
| Kephalis (mixture of 1-ethoxy-4-(ethoxyvinyl)-3,3,5,5,-tetramethylcyclo-1-hexane and 4-)1--ethoxyvinyl)-3,3,5,5-tetramethylcyclohexanone obtained according to Example 2 of the French Pat. No. 1,498,736) | 10 |
| Sandalwood essence | 20 |
| Nor-dehydropatchoulcl | 14 |
| | 1,400 |

EXAMPLE 3

| Concentrate No. 2 | Parts by weight |
|---|---|
| Ylang ylang oil Nossi-bé | 40 |
| Bergamotte peel oil | 240 |
| Lemon peel oil | 120 |
| Benzyl acetate | 100 |
| Hydroxycitronellal | 140 |
| Geranium oil Africa | 60 |
| Petitgrain oil, Grasse | 40 |
| Neroli oil, Grasse | 10 |
| Phenylethyl alcohol | 40 |
| Lauraldehyde C.12 50%, 10% in E.P. | 20 |
| MNA aldehyde C.12 100%, 10% in E.P. | 20 |
| Linalol | 50 |
| C.11 aldehyde 100%, 10% in E.P. | 20 |
| Rose of May absolute | 40 |
| Cyclamen aldehyde | 10 |
| Oak moss absolute | 60 |
| Musk ketone | 60 |
| Coumarin | 80 |
| Jasmine absolute | 60 |
| Hexylcinnamaldehyde | 30 |
| Styrax resinoid No. 1, 50% in E.P. | 30 |
| Kephalis | 50 |
| Sandalwood oil East Indian | 20 |
| Vetiver oil rectified | 20 |
| Methylionone, gamma | 40 |
| Musk ambrette | 90 |
| Cyclohexadecanolide | 30 |
| Nor-dehydropatchoulol | 80 |
| | 1,600 |

We claim:

1. A solid product, nor-dehydropatchoulol, having a melting point of 180° to 183° C. and having the structural formula

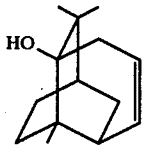

and being substantially free from hydrocarbons, epoxides, alcohols and sesquiterpene ketones occurring in Patchouli Oil.

2. An odoriferous composition in which there has been incorporated the nor-dehydropatchoulol of claim 1.

3. An odoriferous composition according to claim 2, containing from 1 to 5% by weight of said nor-dehydropatchoulol.

4. An organic solvent solution of the product of claim 1.

5. The product of claim 1 in the white crystalline form.

* * * * *